United States Patent [19]

Béziat et al.

[11] Patent Number: 5,053,541
[45] Date of Patent: Oct. 1, 1991

[54] PROCESS FOR THE PREPARATION OF N-ALLYL-META-TRIFLUOROMETHYL ANILINE

[75] Inventors: Yves Béziat, Saint-Clement Lazriviere; Henri-Jean Cristau, Saint Aunes; Jean-Roger Desmurs, Communay; Serge Ratton, La Verpilliere, all of France

[73] Assignee: Rhone-Poulenc Chimie, Courbevoie, France

[21] Appl. No.: 487,718

[22] Filed: Mar. 5, 1990

[30] Foreign Application Priority Data

Mar. 31, 1989 [FR] France ................................ 89 02755

[51] Int. Cl.$^5$ .............................................. C07C 209/10
[52] U.S. Cl. ..................................... 564/405; 502/155; 502/162; 502/167; 564/404
[58] Field of Search ............................... 564/404, 405

[56] References Cited

U.S. PATENT DOCUMENTS

| | | | |
|---|---|---|---|
| 2,040,396 | 5/1936 | Morrell et al. | 564/405 |
| 3,914,311 | 10/1975 | Coulson | 564/405 |
| 4,069,038 | 1/1978 | Teach | 71/95 |
| 4,110,105 | 8/1978 | Teach | 71/95 |
| 4,701,560 | 10/1987 | Regimbeau et al. | 564/404 |
| 4,764,625 | 8/1988 | Turner et al. | 564/405 |

FOREIGN PATENT DOCUMENTS

| | | | |
|---|---|---|---|
| 2305434 | 10/1976 | France . | |
| 1171457 | 8/1986 | Japan | 564/405 |

OTHER PUBLICATIONS

Wilkes et al., "Allyl-Transition Metal System," Angewandte Chemie International Edition, vol. 5, No. 2, pp. 151-164 (Feb. 1966).

Primary Examiner—Glennon H. Hollrah
Assistant Examiner—Susan P. Treanor
Attorney, Agent, or Firm—Finnegan, Henderson, Farabow, Garrett and Dunner

[57] ABSTRACT

A process for the preparation of N-monoallyl-meta-trifluoromethyl aniline, by condensing meta-bromo-trifluoromethyl benzene with allylamine in the presence of a nickel (II) catalyst.

15 Claims, No Drawings

PROCESS FOR THE PREPARATION OF N-ALLYL-META-TRIFLUOROMETHYL ANILINE

BACKGROUND OF THE INVENTION

The present invention relates to a process for the preparation of N-monoallyl-meta-trifluoromethyl aniline which is used extensively as an intermediate in the manufacture of halogenated and N-substituted pyrrolidones.

The preparation of the monoallyl derivative of meta-trifluoromethyl aniline is, for example, an essential step in the synthesis of the herbicide 1-N-meta-trifluoromethylphenyl-3-chloro-4-chloro-methyl-2-pyrrolidone, as described in French Patent No. 2,305,434. However, according to this patent, the preparation of the N-monoallyl-meta-trifluoromethyl aniline intermediate requires allylating a trifluoromethyl aniline in which one of the hydrogen atoms is protected by an acetyl group, in order to prevent the formation of secondary diallylation products which cannot be utilized. Consequently, the process disclosed in this patent takes place in four stages: (1) protection of the amine by acetylation, (2) substitution of the remaining hydrogen by a metal; (3) condensation with an allyl halide; and (4) deacetylation.

However, since multi-stage processes are typically more difficult to implement and less economically advantageous than a single-stage process, the industry has long sought an economical single-stage process for the production of N-monoallyl-meta-trifluoromethyl aniline. Additionally, since meta-trifluoromethyl aniline is a very valuable compound and is desirably conserved, a process is sought which either does not require meta-trifluoromethyl aniline as a starting material or which provides high yields with respect to the meta-trifluoromethyl aniline starting material used.

One solution to this problem is disclosed in U.S. Pat. No. 4,701,560, which describes a single-step process for the allylation of meta-trifluoronethyl aniline comprising reacting an allyl halide, in an aqueous nedium, with a substituted or unsubstituted meta-trifluoronethyl aniline, in the presence of (1) an alkali metal carbonate, an alkali metal hydrogen carbonate or an alkali metal hydroxide, and (2) a catalytic quantity of a tertiary amine. However, in order to produce only small quantities of secondary diallyl products by this method, it is necessary to limit the degree of conversion of the meta-trifluoromethyl aniline by carrying out the reaction in the presence of less than a stoichiometric amount of the allyl halide. For example, the preferred ratio of meta-trifluoromethylaniline to allyl halide is reported to be about 2. Moreover, the yield of the N-monoallylaniline derivative produced, with respect to the meta-trifluoromethyl aniline introduced into the reactor, does not exceed about 40%, which is typically inadequate to obtain good economic profitability from the process.

Accordingly, despite the existence of abundant literature describing the allylation of various anilines, as far as applicants are aware, no process has heretofore been discovered which provides both a high degree of conversion of the starting aniline and a high selectivity for the monosubstituted aniline derivative with respect to the disubstituted aniline derivative.

SUMMARY OF THE INVENTION

The process of the present invention overcomes the deficiencies in the prior art processes noted above by providing a single-step allylation process which does not use meta-trifluoromethyl aniline as a starting material and which provides high selectivity in favor of the monosubstituted aniline derivative.

The allylation process of the present invention provides a process for the preparation of N-monoallyl-meta-trifluoromethyl aniline by condensing allylamine with meta-bromo-trifluoromethyl benzene in the presence of a nickel (II) catalyst, i.e., a catalyst containing nickel in the oxidation state of 2. Additionally, this process is also believed to be useful for the condensation of compounds which are functionally equivalent to the allylamine and the meta-bromo-trifluoromethyl benzene such as, for example, other meta-perfluoroalkyl $(C_1-C_4)$-bromo benzenes and substituted allylamines of up to 6 carbon atoms wherein the substitution occurs on the carbon of the double bond and the carbon atom bonded to the nitrogen atom is preferably in the form of a methylene $(CH_2)$, respectively.

DESCRIPTION OF THE PREFERRED EMBODIMENTS

The preparation of N-monoallyl-meta-trifluoromethyl aniline by a preferred process of the present invention is shown by the following equation:

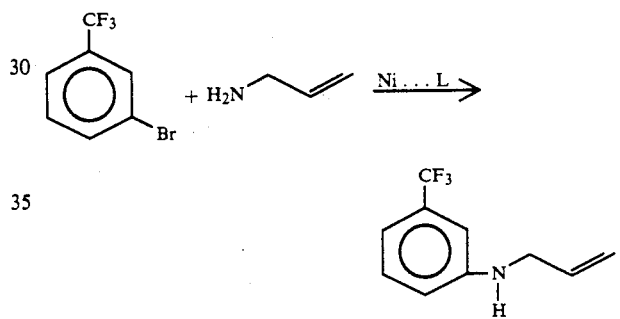

It was unexpectedly discovered that the joint presence of nickel and of a reactant containing an allyl group would enable this reaction to proceed. In fact, it is known from the paper by Wilke, Bogdanovic, Hardt, Heimbach, Keim, Kroner, Oberkirch, Tanaka, Steinrucke, Walter and Zimmermann (Angewandte Chemie, Inter. Edition, 1966, 151-164) that reactants containing an allyl group and nickel form relatively stable π-allyl complexes. It could, therefore, be expected that the nickel would be complexed and that the reaction would stop at this intermediate stage. Contrary to such conventional wisdom, however, applicants surprisingly observed that the reaction was not impeded by the formation of this intermediate, but instead, proceeded favorably and specifically toward formation of an aromatic monoallylamine in which the monoallylamine condensed directly on the aromatic nucleus in the meta position relative to the trifluoromethyl group.

The nickel (II) catalyst is preferably provided in the form of a nickel salt or a nickel salt/ligand complex. Suitable nickel salts may be selected from the group consisting of: nickel dichloride, nickel dibromide, nickel sulfate, nickel dinitrate, nickel diacetate, nickel carlonate, nickel dibenzoate, nickel dihydroxide, nickelocene (or nickel dicyclopentadienyl), and nickel oxide. However, among these nickel salts, the dibromide is most preferred.

The ligands of the catalyst complex are preferably chosen from hydrocarbon ligands containing either nitrogen, phosphorus or oxygen. Suitable nitrogen-containing ligands include: bipyridyl, phenanthroline, and the nitrogenous derivatives of formula (I)

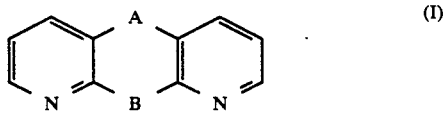

in which A and B each denotes a heteroatom, an alkylidene chain or a covalent bond. Suitable phosphorus-containing ligands include various phosphines such as, for example: orthophenylenediphosphine, 1,2-bis(diphenylphosphine)ethylene, and 1,2-bis(diphenylphosphine)ethane.

The reaction can take place in the presence of an excess of a reactant or it can take place in a solvent. However, the solvent must not react with the starting materials used and must preferably dissolve the reactants. Suitable solvents include aromatic or aliphatic hydrocarbons such as dimethoxyethane, diethylene glycol monoethyl or monomethyl ether, diethylene glycol diethyl or dimethyl ether, ethers, tetrahydrofuran and lower aliphatic alcohols such as ethanol, propanol and butanol.

For better implementation of the invention, it is preferred to employ a quantity of allylamine such that the molar ratio of allylamine to meta-bromo-trifluoromethylbenzene is higher than 1 and more preferably between 1 and 10.

It is also preferred to employ a quantity of catalyst such that the molar ratio of the ligand-complexed catalyst to meta-bromo-trifluoromethyl benzene is from 0.005 to 0.15.

The reaction is preferably carried out at a temperature between ambient temperature and 250° C, and more preferably between 100° C. and 200° C.

The pressure employed will generally be the autogeneous pressure produced by the reaction mixture at the temperature of reaction.

The present invention is further illustrated by the following examples, which should not be considered as limiting the scope of the invention.

EXAMPLE 1

Synthesis of the catalyst dibromobis(o-phenanthroline)nickel(II) or (Phen)$_2$NiBr$_2$ (Phen)$_2$NiBr$_2$ was prepared by the following reaction:

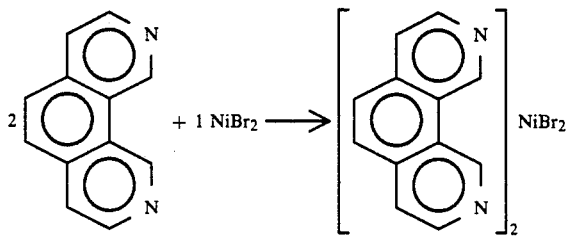

Operating procedure

A solution of 1.35 g (6.8 mmol) of ortho-phenanthroline in 100 cm$^3$ of ethanol was added to a suspension of 0.74 g (3.4 mmol) of anhydrous NiBr$_2$ in 70 cm$^3$ of ethanol at 40° C.

A green color appeared rapidly.

The reaction mixture was then refluxed for 3 hours. Thereafter, the green precipitate formed was filtered off and dried at 80° C. over P$_2$O$_5$ at 0.5 torr for 18 h.

1.48 g (2.6 mmol; 76% yield) of the green solid was recovered.

EXAMPLE 2

Synthesis of the catalyst dibromobis(bipyridine)-nickel(II)=(Bpy)$_2$NiBr$_2$ (Bpy)$_2$NiBr$_2$ was prepared by the following reaction:

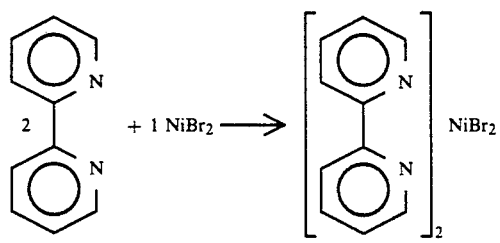

Operating procedure

A solution of 1.11 g (7.14 mmol) of bipyridine in 10 cm$^3$ of ethanol was added to a suspension of 0.78 g (3.57 mmol) of anhydrous NiBr$_2$ in 70 cm$^3$ of ethanol at 40° C.

A green color appeared immediately.

The reaction mixture was then refluxed for 15 hours. The solution was then filtered hot. Thereafter, the green product obtained by cooling the concentrated filtrate was washed with ethanol and dried at 70° C. over P$_2$O$_5$ at 0.5 torr for 24 h.

1.5 g (2.8 mmol; 78.1% yield) of a green solid was recovered.

EXAMPLES 3 TO 7

Synthesis of N-monoallyl-meta-trifluoromethyl aniline

The reactions were carried out in sealed glass tubes capable of withstanding a pressure of approximately 50 bars.

The solid catalyst was weighed and then introduced into the tube through a funnel. The liquid reactants were introduced by volume with the aid of a pipette.

The tube was cooled to −40° C. in ethanol and then sealed.

The sealed tube was then introduced into a steel autoclave, which was placed in a heated agitated jacket.

At the end of the reaction, the tube was cooled and then unsealed.

15 ml of 1N sodium hydroxide was then added to the contents of the tube and the mixture was extracted with ether (3×10 ml).

The organic phase was then filtered through sintered glass, treated with celite and then analyzed by GPC.

COMPARATIVE EXAMPLE

A comparative test was performed in the same conditions as in Example 3, using a catalyst based on nickel in the zero oxidation state, Ni[P(C$_6$H$_5$)$_3$]$_4$.

The amounts of reactants, solvent, catalyst, reactant conversion, and product yield for Examples 3–7 and the Comparative Example are shown in Table 1. With respect to the conversions and yield displayed, the following abbreviations are used:

$$TT = \frac{\text{moles of reactant transformed}}{\text{moles of reactant introduced}}$$

$$RT = \frac{\text{moles of desired product produced}}{\text{moles of reactant transformed}}$$

TABLE 1

| Examples | ![CF3-phenyl-Br] | H₂N⌒ | Solvent | Catalyst mol % | Conditions | TT (CF3-phenyl-Br) | RT (CF3-phenyl-N-allyl) |
|---|---|---|---|---|---|---|---|
| 3 | 0.45 g | 1.15 g | Dimethyl ether 1.2 ml | NiBr₂ 3.5% | 18 h, 160° C. | 19% | 100% |
| 4 | 0.45 g | 1.15 g | Dimethyl ether 1.2 ml | NiBr₂ 11% | 18 h, 160° C. | 23% | 100% |
| 5 | 0.45 g | 1.15 g | Dimethyl ether 1.2 ml | Ex 1 11% | 18 h, 160° C. | 30% | 100% |
| 6 | 0.45 g | 1.15 g | Dimethyl ether 1.2 ml | Ex 2 11% | 18 h, 160° C. | 45% | 100% |
| 7 | 0.45 g | 1.15 g | Ethanol 1.2 ml | Ex 2 3.5% | 18 h, 160° C. | 82% | 84% |
| COMPARATIVE | 0.45 g | 1.15 g | Dimethyl ether 1.2 ml | Ni[P(C₆H₅)₃]₄ 3.5% | 18 h, 160° C. | 9% | 45% |

EXAMPLES 8 TO 10

Synthesis of the catalyst dibromo-1,2-bis(diphenylphosphine)-ethylene nickel

Dibromo-1,2-bis(diphenylphosphine)ethylene nickel was prepared by the following reaction:

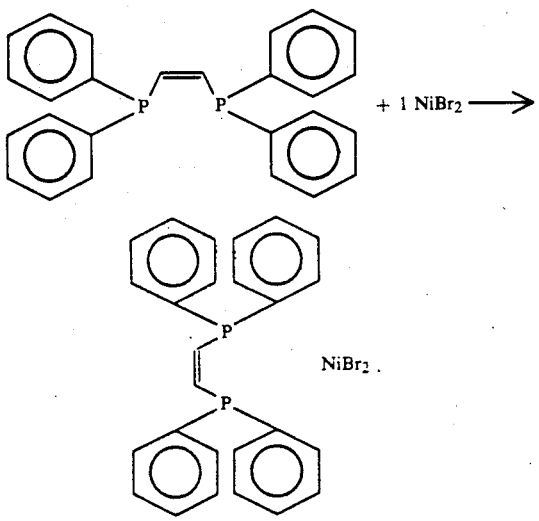

0.55 g of NiBr₂.3H₂O was introduced into 1 ml of ethanol. Independently, a mixture of 0.8 g of ethylenediphosphine dissolved in 10 ml of ethanol and 15 ml of toluene was prepared. The mixture was heated to reflux and then the nickel bromide solution was added. A brown precipitate of the ethylenediphosphine-NiBr₂ complex was formed. The synthesis yield attained 88%.

The catalyst was isolated and 0.07 millimole was introduced into a sealed tube, as in Example 3, in the presence of 0.002 mole of meta-bromo-trifluoromethylbenzene, 0.020 mole of allylamine and 1.2 ml of ethanol. The mixture was heated to 160° C. and maintained at that temperature for 12 hours.

In Example 9, Example 8 was reproduced by synthesizing the catalyst directly in the sealed glass tube. In all other respects, the reaction conditions were identical with those of Example 8.

The amounts of reactants, solvent, catalyst, reactant conversions and product yields for Examples 8-10 are shown in Table 2.

TABLE 2

| Examples | ![CF3-phenyl-Br] | H₂N⌒ | Solvent | Catalyst | Conditions | TT (CF3-phenyl-Br) | RT (CF3-phenyl-N-allyl) |
|---|---|---|---|---|---|---|---|
| 8 | 0.45 g | 1.15 g | Ethanol 1.2 ml | Ethylenediphosphine NiBr₂ 3.5% | 12 h, 160° C. | 34% | 50% |

TABLE 2-continued

| Examples | CF$_3$–C$_6$H$_4$–Br | H$_2$N–allyl | Solvent | Catalyst | Conditions | TT (CF$_3$–C$_6$H$_4$–Br) | RT (CF$_3$–C$_6$H$_4$–N-allyl) |
| --- | --- | --- | --- | --- | --- | --- | --- |
| 9 | 0.45 g | 1.15 g | Ethanol 1.2 ml | Ethylenediphosphine NiBr$_2$ 3.5% | 12 h, 160° C. | 35% | 40% |
| 10 | 0.45 g | 1.15 g | Ethanol 1.2 ml | NiBr$_2$ 3.5% | 12 h, 160° C. | 19% | 100% |

What is claimed is:

1. A process for the preparation of N-monoallyl-meta-trifluoromethyl aniline, which comprises condensing allylamine with meta-bromo-trifluoromethyl benzene in the presence of a nickel (II) catalyst.

2. The process as claimed in claim 1, wherein the nickel (II) catalyst is a nickel (II) salt selected from the group consisting of nickel dichloride, nickel dibromide, nickel sulfate, nickel dinitrate, nickel diacetate, nickel carbonate, nickel dibenzoate, nickel dihydroxide, nickelocene, and nickel oxide.

3. The process as claimed in claim 1, wherein the nickel (II) catalyst is nickel dibromide.

4. The process as claimed in claim 1, wherein the nickel (II) catalyst is a complex of a nickel salt with at least one ligand.

5. The process as claimed in claim 4, wherein the nickel salt is selected from the group consisting of nickel dichloride, nickel dibromide, nickel sulfate, nickel dinitrate, nickel diacetate, nickel carbonate, nickel dibenzoate, nickel dihydroxide, nickelocene, and nickel oxide.

6. The process as claimed in claim 4, wherein the ligand is selected from hydrocarbon ligands containing at least one atom selected from the group consisting of nitrogen, phosphorous and oxygen.

7. The process as claimed in claim 4, wherein the ligand is selected from the group consisting of bipyridyl, phenanthroline, and the nitrogenous derivatives of

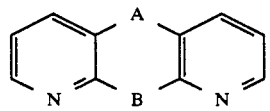

in which A and B each denotes a heteroatom, an alkylidene chain or a covalent bond.

8. The process as claimed in claim 4, wherein the ligand is selected from the group consisting of ortho-phenylenediphosphine, 1,2-bis(diphenylphosphine)ethylene and 1,2-bis(diphenylphosphine)ethane.

9. The process as claimed in claim 4, wherein the nickel salt is nickel dibromide and the ligand is bipyridyl.

10. The process as claimed in claim 1, wherein the condensation takes place in the presence of a solvent selected from the group consisting of dimethoxyethane, diethylene glycol monoethyl ether, diethylene glycol monomethyl ether, diethylene glycol diethyl ether, diethylene glycol dimethyl ether, tetrahydrofuran and a lower aliphatic alcohol.

11. The process as claimed in claim 10, wherein the lower aliphatic alcohol is selected from the group consisting of ethanol, propanol and butanol.

12. The process as claimed in claim 1, wherein the molar ratio of allylamine to meta-bromo-trifluoromethyl benzene is in the range of from 1 to 10.

13. The process as claimed in claim 4, wherein the molar ratio of the nickel (II) catalyst complex to meta-bromo-trifluoromethyl benzene is in the range of from 0.005 to 0.15.

14. The process as claimed in claim 1, wherein the reaction temperature is between 100° C. and 200° C.

15. A process for the preparation of N-monoallyl-meta-trifluoromethyl aniline comprising condensing allylamine with meta-bromo-trifluoromethyl benzene in the presence of a catalyst comprising a ligand-complexed nickel (II) salt, wherein said ligand is selected from the group consisting of hydrocarbon ligands containing at least one atom selected from nitrogen, phosphorous and oxygen, and said nickel (II) salt is selected from the group consisting of nickel dichloride, nickel dibromide, nickel sulfate, nickel dinitrate, nickel diacetate, nickel carbonate, nickel dibenzoate, nickel dihydroxide, nickelocene, and nickel oxide, and wherein the molar ratio of allylamine to meta-bromo-trifluoromethyl benzene is from 1 to 10 and the molar ratio of the ligand-complexed catalyst to meta-bromo-trifluoromethyl benzene is from 0.005 to 0.15.

* * * * *